United States Patent [19]

Lindegren

[11] Patent Number: 5,769,077
[45] Date of Patent: Jun. 23, 1998

[54] MULTI-CONTACT IMPLANTABLE ELECTRODE CABLE WITH A RESORBABLE STIFFENING ELEMENT

[75] Inventor: Ulf Lindegren, Enskede, Sweden

[73] Assignee: Pacesetter AB, Solna, Sweden

[21] Appl. No.: 771,660

[22] Filed: Dec. 23, 1996

[30] Foreign Application Priority Data

Dec. 28, 1995 [SE] Sweden ................................. 9504675

[51] Int. Cl.[6] ..................................................... A61N 1/05
[52] U.S. Cl. ........................................... 128/642; 607/122
[58] Field of Search ............................ 128/642; 607/122, 607/123, 119, 125, 115, 116

[56] References Cited

U.S. PATENT DOCUMENTS

| | | |
|---|---|---|
| 4,258,724 | 3/1981 | Balat et al. . |
| 4,522,212 | 6/1985 | Gelinas et al. . |
| 4,699,147 | 10/1987 | Chilson et al. . |
| 5,476,495 | 12/1995 | Kordis et al. . |
| 5,653,742 | 8/1997 | Parker et al. ........................ 607/137 |

FOREIGN PATENT DOCUMENTS 0 085 967   8/1983   European Pat. Off. .

Primary Examiner—Scott M. Getzow
Attorney, Agent, or Firm—Hill, Steadman & Simpson

[57] ABSTRACT

An electrode device which has a proximal end and distal end, contains of a number of thin, insulated electrical conductors each with a proximal end and a distal end, the conductors being equipped with implantable electrode contacts means which are electrically connected to the conductors. These contacts are designed to be brought into electrical contact with tissue in one or more cavities in a human body. Each conductor in the cable device is supported by a pre-shaped stiffening element which runs along and is connected to the conductor, made of an elastic polymer material, resorbable in vivo, which is biodegradable and biocompatible. The stiffening element imparts an arched shaped to the conductor, at least in the area in which its contact is located, to cause the contact to press against the adjacent cavity wall. The cable device also includes a longitudinal channel in which a stylet can be inserted for temporary, linear stretching of the cable device and the arched sections of its conductors.

10 Claims, 2 Drawing Sheets

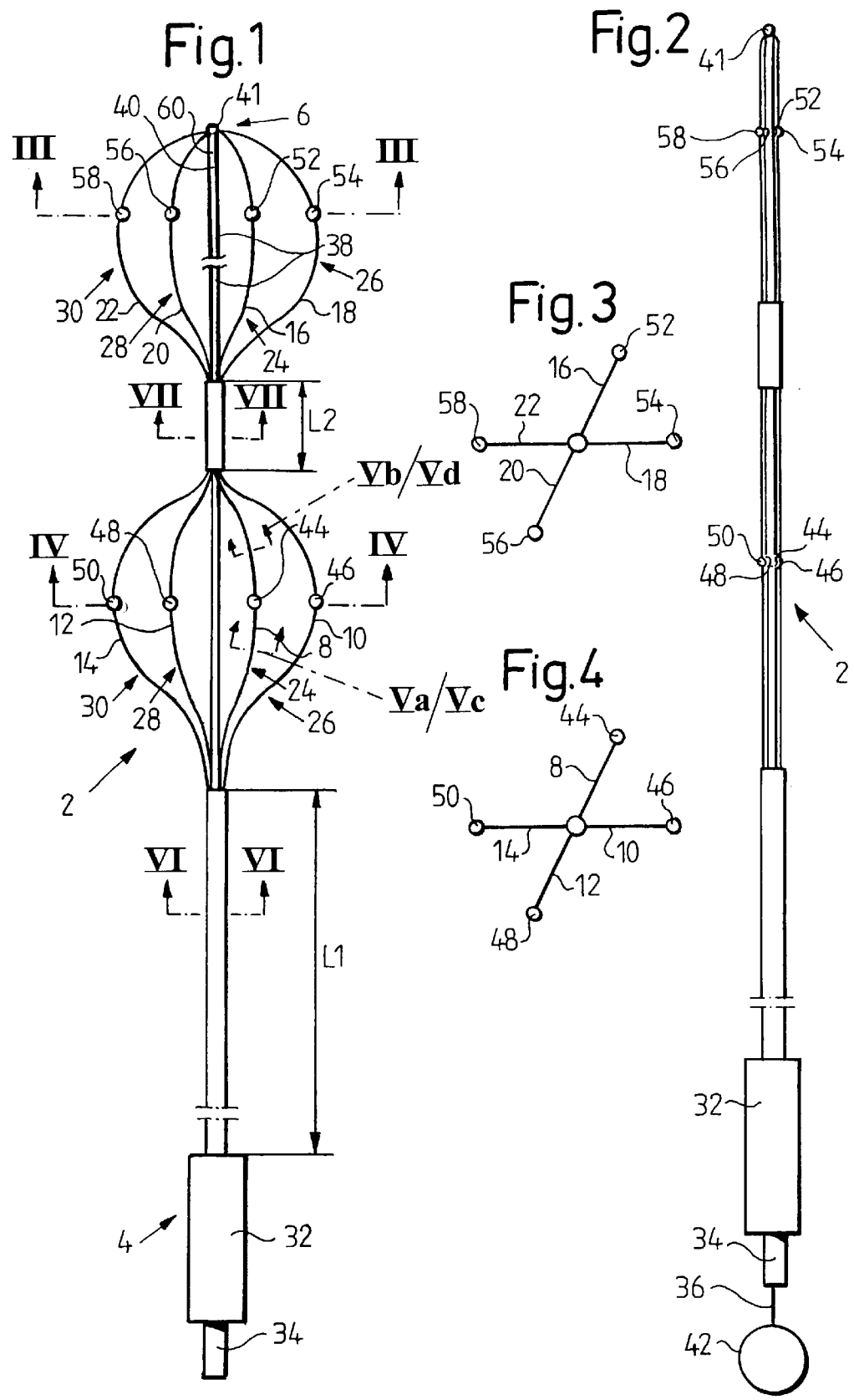

MULTI-CONTACT IMPLANTABLE ELECTRODE CABLE WITH A RESORBABLE STIFFENING ELEMENT

BACKGROUND OF THE INVENTION

1. Field of the Invention

The present invention relates to an electrode cable device of the type having a proximal end and a distal end with one or more thin, insulated electrical conductors each having a proximal end and a distal end, at least one of the conductors having at least one implantable electrode contact in electrical connection with the conductor and intended for permanent electrical contact with the wall of a cavity in a human body. The cable device of this type is devised so the electrode contact can be kept pressed, by means of pre-tensioning, against an area of the wall forming the cavity in the body. The body cavity can e.g. be an atrium or a ventricle of the heart.

2. Description of the Prior Art

An electrode cable device of the aforementioned kind is especially designed for introduction into a patient's heart and for anchoring the device's electrode contact or contacts in the ventricle and/or atrium. Such an electrode cable device is usually introduced into the heart via a vein, and the electrode contacts are usually anchored in the right ventricle or atrium of the heart. The proximal end of the electrode cable device is intended for connection to a heart stimulator which has been implanted into the body. The electrode cable device can then be used for carrying electrical impulses from the heart stimulator to the heart, via the implantable electrode contacts, and/or for sensing and registering heart signals.

U.S. Pat. No. 4,522,212 describes an endocardiac electrode device having at least three curved spring wires designed for introduction into the heart, each curved spring wire carrying an array of electrodes situated to form a characteristic geometric pattern across the ventricular contact area covered by the spring wires. The active electrode arrays achieve recognizable patterns when inside a heart ventricle and can be viewed with a fluoroscope. The electrodes are located in relation to each other and on the spring wires so the wires, with their electrodes, can easily be squeezed into a narrow spring wire bundle which fits inside a catheter during the catheter's introduction into the heart. The catheter can then be retracted slightly, exposing electrodes on the curved spring wires which spring outwardly into a balloon-like shape inside the heart ventricle. The curved spring wires consist of curved metal arches with external insulation along their entire length, except at the points at which electrodes are attached. When the electrode cable device has been implanted inside the heart, the spring wires retain their original pre-tensioning, thereby exerting constant pre-tensioning pressure on the electrodes.

U.S. Pat. No. 4,699,147 describes a probe, equipped with a plurality of electrodes for intraventricular heart catheterization. The probe has a catheter with an open, proximal end, an open distal end and four elongate conductor devices, with a distal end section and a proximal end section, inside the catheter and projecting beyond the open, proximal end of the catheter. Each conductor device has a tubular sleeve, six insulated wirelike conductors inside the sleeve and a stiff but flexible central core wire arranged inside the sleeve and extending along most of the sleeve's length. A proximal contact is mounted on each tubular sleeve. The distal end section of each conductor device carries six separate shell electrodes connected to each wire-like conductor. The section of each core wire at the distal end section of the conductor devices can be made to assume a desired configuration after the distal end sections of the conductor devices are moved from a retracted position inside the catheter to a position in which the distal end sections project outside the catheter, and the core wires can be made to assume a desired configuration in order to jointly form an elliptical wire sleeve. The catheter is designed for introduction into an artery or vein and placement of its distal end opening in a heart ventricle. From this end opening, the distal end sections of the conductor devices can be extended to form the elliptical wire shell and then rotated in stages while electrical potentials are measured and recorded at different points on the surface of endocardiac ventricular wall in contact with the shell electrodes. Even in this known type of electrode cable probe, the core wires retain their elliptical configuration from the time they are able to bulge outwardly, as a result of their pre-tensioned elliptical shaping, and make contact with the ventricular wall of the heart. The shell electrodes are kept permanently pressed against the ventricular wall of the heart as a result of the spring force residing in the core wires of the conductor devices and cannot be pulled out of same. If one of the electrodes were to fracture after implantation, the pre-shaping can cause the electrode to penetrate the heart wall, with possibly fatal consequences.

SUMMARY OF THE INVENTION

An object of the present invention is to provide an electrode device which allows positioning and anchoring of a number of small electrode contacts at a corresponding number of sites in the ventricle and atrium of a heart. It is a further object to provide such an electrode device which applies the electrode contacts against internal surface areas of the walls of the ventricle and atrium initially with a given pressure (pre-tensioning) exerted by pressure-exerting stiffening elements, after which, following a given period of time when the electrode elements have become anchored/embedded in heart tissue, the electrode device firmly seats the electrode contacts in the respective heart wall area without the continued exertion of any residual pressure by any stiffening arrangement.

The above objects are achieved in accordance with the principles of the present invention in an electrode device having a stiffening element which is used at an initial stage of electrode implantation to keep the electrode contacts pressed against the respective cavity wall, and which successively degrades and dissolves after the requisite anchoring/embedding of the electrode contacts has occurred, when the stiffening element is no longer needed.

A related object of the invention is to select a material for the stiffening element which is slightly bendable but which initially is stiff enough to hold the electrode contacts in place against tissue and which, by the action of body fluids, gradually loses its stiffening properties over a given, appropriate period of time.

A primary feature of the inventive electrode cable device is that its conductor, or each conductor in a multi-electrode version, is supported by an elongate, pre-shaped stiffening element, connected to and running along the conductor, made of abendable material which is resorbable in vivo. This stiffening element is devised and arranged to impart an arched or helical shape to at least the section of the conductor on which its contact is located. The electrode cable device also has a channel, which extends longitudinally through the device, into which a stylet can be removably inserted to permit temporary, substantially linear straightening of the cable device and its conductor's arched or helical section.

The bendable material, which is resorbable in vivo, is, according to the invention, a material which is biodegradable or soluble within an appropriate period of time after it comes into contact with blood. The resorbable or degradable material is preferably selected from the groups of proteins/amino acid polymers, polyhydroxycarboxyl acids and/or carbohydrate polymers. The proteins/amino acid polymers group can contain gelatin, collagen, polyserine, polythreonine, polyphenylalanine or the like. The polyhydroxycarboxyl acids group can contain polylactides and/or polyglycolides. The carbohydrate polymers group can contain dextran, starch, hyaluronic acid, cellulose or the like.

Breakdown or degradation time for the material resorbable in vivo should be at least several hours but should generally be on the order of about 24 hours to three to four weeks or, in some instances, months.

In an embodiment in which the electrode cable device has at least one pair (preferably two pairs) of thin, insulated electrical conductors, each conductor in each pair can have an electrode contact, serving as a microelectrode, arranged on a convex, arching section of its conductor, which bulges out from the center line (longitudinal axis) of the cable device, the conductors in each pair of conductors arching outwardly in opposite directions.

With a cable device devised in this way, both conductors, equipped with stiffening elements, in each conductor pair form a convex position-retaining means in the body cavity in which the conductor pair is located.

When the electrode cable device according to the invention is to be used for placing groups of electrode contacts in separate body cavities, such as the atrium and ventricle of a heart, a version is used in which two groups of electrode contacts are disposed in their respective cavity (chamber) by two longitudinally separate contact areas of the device. Each contact area is intended for a separate body cavity. When such a cable device has four pairs of insulated electrical conductors, the electrode contacts can suitably be distributed among the contact areas with the contacts for two pairs of conductors respectively disposed in two contact areas.

When the electrode contact means are grouped for activity in different contact areas (in different body cavities), the electrical conductors plus attendant stiffening elements form bundled cable strings within the cable section in which the conductors have no contacts, e.g. between the above-mentioned contact areas. The pre-shaped stiffening elements, which are connected to the conductors and extend along same, can be devised in different ways. In a particularly simple embodiment, each stiffening element is a tubular sleeve on the exterior of the conductor. Alternatively each stiffening element can be a continuous band-shaped or wire-like element running along and attached to the conductor.

A channel for temporarily receiving a stylet can be formed by a longitudinal channel inside the cable string sections, with a round cross-section.

The distal ends of the conductors in an anterior contact area are appropriately connected to the channel at the distal end of the cable device.

The pre-shaped stiffening element running along each conductor, as described above, is made of a bendable material which is resorbable in vivo. This material should be biodegradable and dissolve in the body within an appropriate period of time after being in contact with blood. The period of time must be such that the respective electrode contact has time to become embedded in the tissue of the wall of the respective body cavity before the stiffening element degrades and dissolves through the action of blood. The degradation and removal by the blood of the stiffening element after a given period of time accordingly completely removes stiffening element along each conductor after this given period of time during which the electrode contact has become embedded into the wall of the adjacent body cavity, thereby eliminating the continued presence of a stiffening, pressure-application means for the electrode contact after it is no longer needed, thereby conveying a major advantage.

The risk of a future fracture of the arched, electrode contact-carrying wires causing fatal consequences, as is present with the aforementioned known types of electrode contact devices is accordingly avoided.

This possibility obviously poses a life-threatening risk to a patient in whom a conventional pre-shaped conductor is implanted, since fatigue fracture of a spring-biased wire, in the heart as an "electrode holder", could have fatal consequences if any part of the broken wire spring penetrates the wall of the ventricle or atrium, an event which may lead to death caused by internal bleeding.

DESCRIPTION OF THE DRAWINGS

FIG. 1 is a schematic lateral view of an electrode cable device constructed in accordance with the principles of the present invention, equipped with a number of electrode contacts, in its implantated state with the electrode contacts bulging outwardly.

FIG. 2 shows the electrode cable device according to FIG. 1 with the electrode contacts radially "collapsed" by the insertion of an axial stylet into an axial channel inside the electrode cable device, stretching the cable device axially and longitudinally.

FIGS. 3 and 4 respectively show cross-sections through the electrode device at section lines 111—111 and IV—IV in FIG. 1.

DESCRIPTION OF THE PREFERRED EMBODIMENTS

Figure 5A:
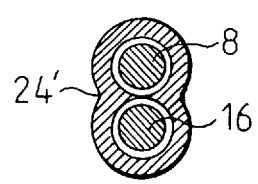
FIGS. 5a and 5b respectively show cross-sections at Va and Vb in FIG. 1.
Figure 5B:
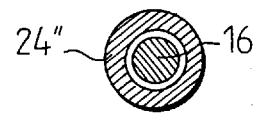
Figure 5C:
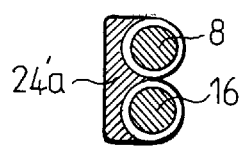
FIGS. 5c and 5d respectively show cross-sections through another embodiment of a stiffening element as if this embodiment were present at Vc and Vd in FIG. 1.
Figure 5D:
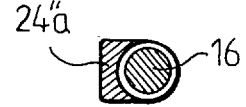

FIG. 1 schematically depicts an electrode cable device 2 according to the invention. The cable device has a proximal end 4 and a distal end 6 and, in this instance, eight thin, flexible, insulated electrical conductors 8, 10, 12, 14, 16, 18, 20 and 22, each with a proximal end and a distal end. Each conductor in the electrode cable device 2 is supported by an associated, elongate stiffening element 24, 26, 28 and 30, connected to the conductor. Each such stiffening element 24–30 extends along at least part of the conductors. In the illustrated instance, the stiffening element 24 passes axially through the electrode cable device 2, and the stiffening element 24 accordingly supports both the electrical conductors 8 and 16. In the corresponding manner, the stiffening element 26 supports both the insulated electrical conductors 10 and 18. The stiffening elements 28 and 30 correspondingly support the electrical conductors 12 and 20, and 14 and 22, respectively.

The proximal ends of the pre-shaped stiffening elements 24–30 are connected to one end of a common electrode cable connector 32 on the proximal end 4 of the electrode cable device 2. The electrode cable connector 32 is for connecting the electrode cable device 2 to a heart stimulator or pacemaker (not shown). At the lower end, as shown in FIG. 1, the connector 32 is equipped with a stylet orifice 34 through which a stylet 36, shown in FIG. 2, can be inserted into a channel 38 in the electrode cable device 2. The channel 38 extends axially along the length of the cable device 2 from the connector 32 to an electrode contact 41 at the distal end 6 of the cable device 2. The channel 38 can be e.g. a thin, relatively stiff but flexible tube having a longitudinal channel 40 into which the stylet 36 can be introduced in order to achieve axial stretching of the electrode cable device 2, from the state shown in FIG. 1 to a substantially straight state shown in FIG. 2, making it much easier to introduce the electrode cable device 2 (preferably via a vein) into the heart. The stylet 36 is manipulated during its insertion in and out of the channel 38 with fixed handle 42 at the proximal end of the stylet 36.

In this instance, each of the thin, insulated electrical conductors 8–22 is electrically connected to an associated implantable electrode contact 44, 46, 48, 50, 52, 54, 56 and 58. The electrode contacts 44–58, devised as microelectrodes, are intended to be brought into permanent electrical contact with tissue in the wall of the cavity in a human body in which they have been implanted.

The electrode cable device 2 shown in FIGS. 1 and 2 is designed, preferably, for transmitting electrical signals between a heart stimulator, connected to the connector 32, and the two cavities in a human heart in which the contacts 44–58 are to be implanted to achieve electrical contact. The four electrode contacts 52, 54, 56 and 58 are arrayed in a first contact area of the cable device 2, whereas the other four electrode contacts 44, 46, 48 and 50 are arrayed in a second contact area, separate from the first contact area along the longitudinal direction of the cable device 2, which is closer to the proximal end 4 of the cable device 2 than the first contact area (with contacts 52–58).

In the illustrated instance, the first contact area with the contacts 52–58 is intended for the left ventricle in a heart, whereas the second contact area with the contacts 44–50 is intended for the left atrium of a heart.

The electrode contacts 44–50 and 52–58, respectively, are intended to achieve permanent electrical contact with tissue in the wall of the cavity in which they are arranged. In order to achieve this desired permanent electrical contact with the wall of the cavity in question, the electrode contacts are kept, at an initial stage of their implantation, pressed against the wall of the cavity with pressure exerted by pre-shaped stiffening element 24, 26, 28 and 30, running along the conductors, which support the conductors 8–22. These four elongate stiffening elements 24–50, connected to and running along the conductors, are made of a bendable material which is resorbable in vivo. The stiffening elements 24–30 are pre-shaped in such a way that they impart an arched shape to their respective conductors, at least in the parts of the conductors in which the contacts 44–58 are located. The stiffening elements 24–30 and the electrical conductors 8–22 supported by them are arranged in pairs so they lie on a common plane, the conductors in each such conductor pair arching outwardly in opposite directions. This circumstance is not very apparent in FIG. 1 but is clearly depicted in the sectional views in FIGS. 3 and 4, showing the III—III and IV—IV section lines in FIG. 1.

The electrode cable device 2 shown in FIG. 1 therefore contains four pairs of insulated electrical conductors, viz. pairs 8–12, 10–14, 16–20 and 18–22. The conductor pairs 16–20 and 18–20 have their electrode contacts 52–58 located in the first contact area of the cable device 2, in which section III—III is located, whereas the other two conductor pairs 8–12 and 10–14 have their electrode contact means 44–50 located in the second contact area, in which section IV—IV is located.

The electrical conductors B-22 with their associated stiffening elements 24–30 made of resorbable material and the channel 38 for the stylet 36 are bundled into a single string in a first cable section LI, located between the proximal end 4 of the cable device 2, and the second contact area (containing the IV—IV section), located between the two axially separate contact areas.

The stiffening element, such as the element 24, for each insulated electrical conductor, such as conductors 8 and 16, is formed by a sleeve, enclosing the conductor, made of resorbable material, the sleeve being casing-like or tubular. At section V$a$ in FIG. 1, the two conductors 8 and 16 run parallel to each other, the stiffening element 24' being sleeve-like and displaying the figure eight-shaped cross-section shown in FIG. 5$a$. In FIG. 5$b$, which shows the section V$b$, the stiffening element 24" can have a circular, tubular shape, since only a single conductor 16 is involved, since the conductor 8 only extends to the electrode contact 44.

As an alternative to a tubular or sleeve-shaped structure, the stiffening elements 24, 26, 28 and 30 for each insulated electrical conductor could be formed by a band-shaped or wire-shaped stiffening element running along and attached to the conductor. FIGS. 5$c$ and 5$d$ show examples of such a band-shaped stiffening element, respectively designated 24$a'$ and 24$a''$, the stiffening element is broader at section V$c$ shown in FIG. 5$c$ than at section V$d$ shown in FIG. 5$d$.

Figure 6:
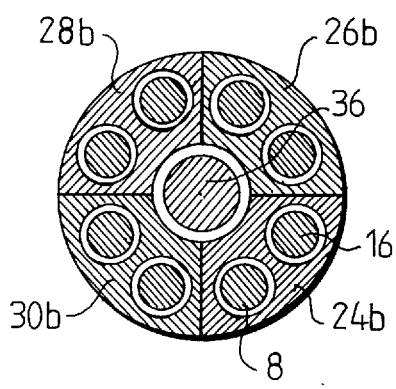
FIGS. 6 and 7 respectively show cross-sections at VI—VI and VII—VII in FIG. 1.

FIG. 6 shows a cross-section VI—VI through the posterior cable section L1, bundled into a single cable string, in FIG. 1. Here, the stiffening element 24$b$ for e.g. the conductors 8 and 16, is devised as a string-like element with an approximately quarter circle-shaped cross-section, the three other stiffening elements 26$b$, 28$b$ and 30$b$ displaying a corresponding quarter circle-shaped cross-section, so the four string-shaped elements 24$b$, 26$b$, 28$b$ and 30$b$ jointly give the cable device a circular cross-section for the posterior cable section L1.

The channel 38 for the stylet 36 then is a longitudinal channel 40 inside the cable section LI with a cross-section which, in total, is circular.

Figure 7:
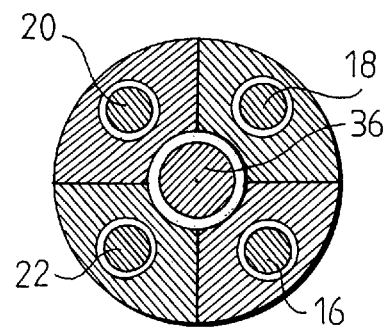

FIG. 7 shows a corresponding cross-section VII—VII through the anterior channel section L2. Since this channel section only contains the conductors 16, 18, 20 and 22 for the electrode contacts 52, 54, 56 and 58, the string-shaped channel section L2 acquires the cross-sectional shape shown in FIG. 7 with only one conductor in each quarter circle string.

As shown at the top of FIG. 1, the distal ends of the conductors 16, 18, 20 and 22 in the anterior, first contact area are connected to the channel 38 located on the distal end 60 of the cable device 2.

Although modifications and changes may be suggested by those skilled in the art, it is the intention of the inventor to embody within the patent warranted hereon all changes and modifications as reasonably and properly come within the scope of his contribution to the art.

I claim as my invention:

1. An implantable electrode cable device having a proximal end and a distal end and comprising at least one thin, insulated electrical conductor with a proximal end and a distal end, said conductor carrying at least one electrode contact electrically connected to the conductor, adapted for permanent electrical contact with tissue of a cavity in a human body, elongate pre-shaped stiffening means connected to and running along the conductor, made of an bendable material which is resorbable in vivo, for imparting an arch to at least a section of the conductor in an area in which said electrode contact is disposed until said material is resorbed and a longitudinal channel for receiving a stylet for temporary, substantially linear stretching of the cable device and said arch of said conductor.

2. A cable device according to claim 1, comprising at least one pair of said thin, insulated electrical conductors, each conductor pair carrying a microelectrode as said electrode contact arranged on a convex, curving section of the conductor arching outwardly a center line of said cable device, each conductor in said conductor pair arching outwardly in opposite directions.

3. A cable device according to claim 1 comprising at least two pairs of said thin, insulated electrical conductors, including a first conductor pair associated electrode contacts in a first contact area of the cable device, and a second conductor pair having associated electrode contacts in a second contact area, longitudinally separate from the first contact area the second contact area being closer to the proximal end of the cable device than the first contact area.

4. A cable device according to claim 3, comprising four pairs of said thin, insulated electrical conductors, two of the conductor pairs having electrode contacts located in the first contact area, and another two conductor pairs having electrode contacts in the second contact area.

5. A cable device according to claim 3 wherein said thin, insulated electrical conductors, and said stiffening means are bundled surrounding said channel into a single cable string in a first cable section, located between the proximal end of the cable device and the second contact area, and a second, anterior cable section, located between the first and the second contact area.

6. A cable device according to claim 5, wherein the stiffening means for the conductors in each conductor pair consists of a string-shaped element at least partially enclosing both conductors, each string-shaped element having a cross-section for producing a total cross-section of the cable device which is circular.

7. A cable device according to claim 6, the channel consists of a longitudinal channel inside said string-shaped elements and having a circular cross-section.

8. A cable device according to claim 3 wherein the distal ends of the conductors in the anterior, first contact area are connected to an end of the channel located at the distal end of the cable device.

9. A cable device according to claim 1 wherein the stiffening means for each insulated electrical conductor consists of a tubular sleeve enclosing the conductor.

10. A cable device according to claim 1 wherein the stiffening means for each insulated electrical conductor consists of a band-shaped element running along and attached to the conductor.

* * * * *